United States Patent
Song et al.

(10) Patent No.: US 12,269,161 B2
(45) Date of Patent: Apr. 8, 2025

(54) MULTI-DEGREE-OF-FREEDOM MYOELECTRIC ARTIFICIAL HAND CONTROL SYSTEM AND METHOD FOR USING SAME

(71) Applicant: Southeast University, Jiangsu (CN)

(72) Inventors: Aiguo Song, Jiangsu (CN); Xuhui Hu, Jiangsu (CN); Zhikai Wei, Jiangsu (CN); Huijun Li, Jiangsu (CN); Baoguo Xu, Jiangsu (CN); Hong Zeng, Jiangsu (CN)

(73) Assignee: SOUTHEAST UNIVERSITY, Jiangsu (CN)

( * ) Notice: Subject to any disclaimer, the term of this patent is extended or adjusted under 35 U.S.C. 154(b) by 653 days.

(21) Appl. No.: 17/628,753

(22) PCT Filed: Jun. 3, 2020

(86) PCT No.: PCT/CN2020/094132
§ 371 (c)(1),
(2) Date: Jan. 20, 2022

(87) PCT Pub. No.: WO2021/174705
PCT Pub. Date: Sep. 10, 2021

(65) Prior Publication Data
US 2022/0355469 A1  Nov. 10, 2022

(30) Foreign Application Priority Data
Mar. 3, 2020 (CN) .......................... 202010139635.5

(51) Int. Cl.
*A61F 2/68* (2006.01)
*A61F 2/72* (2006.01)
(Continued)

(52) U.S. Cl.
CPC ............... *B25J 9/1602* (2013.01); *A61F 2/72* (2013.01); *B60K 6/365* (2013.01); *A61F 2002/6836* (2013.01)

(58) Field of Classification Search
CPC ........ B25J 9/1602; B25J 9/1612; B25J 17/02; B25J 17/0283; A61F 2/72; A61F 2/585; A61B 5/389; A61B 5/4851; B60K 9/365
See application file for complete search history.

(56) References Cited

U.S. PATENT DOCUMENTS

| 4,807,486 A * | 2/1989 | Akeel ................. B25J 17/0283 901/29 |
| 5,197,846 A * | 3/1993 | Uno ..................... B25J 19/0016 414/731 |

(Continued)

FOREIGN PATENT DOCUMENTS

| CN | 103892945 A | 7/2014 |
| CN | 104997579 A | 10/2015 |

(Continued)

OTHER PUBLICATIONS

English translation of Description section of Chinese patent CN103892945. (Year: 2014).*

(Continued)

*Primary Examiner* — Ann Hu
(74) *Attorney, Agent, or Firm* — MUNCY, GEISSLER, OLDS & LOWE. P.C.

(57) ABSTRACT

Provided are a multi-degree-of-freedom myoelectric artificial hand control system and a method for using same. The system comprises a robotic hand, a robotic wrist (2), a stump receiving cavity (1) and a data processor (3), wherein the robotic hand and the stump receiving cavity (1) are respectively mounted on two ends of the robotic wrist (2); a multi-channel myoelectric array electrode oversleeve, a control unit circuit board, and a battery are connected in the (Continued)

stump receiving cavity (1); and the other end of the control unit circuit board is connected to the robotic hand and the robotic wrist (2). The method for using the system comprises the following steps: (S1) a user wearing a multi-channel myoelectric array electrode oversleeve, and connecting a battery and a control unit circuit board; (S2) the user completing a gesture, collecting a surface electromyography signal and then uploading same to a data processor (3); (S3) the data processor (3) receiving the surface electromyography signal and inputting same into a neural network algorithm to generate a gesture prediction model; and (S4) the user controlling the multi-degree-of-freedom movement of the robotic wrist (2) and the robotic hand. By means of the system, continuous gestures and the gesture strength thereof can be identified, and multi-degree-of-freedom gestures can be made.

7 Claims, 5 Drawing Sheets

(51) Int. Cl.
*B25J 9/16* (2006.01)
*B60K 6/365* (2007.10)

(56) References Cited

U.S. PATENT DOCUMENTS

| | | | |
|---|---|---|---|
| 5,413,611 A | 5/1995 | Haslam, II et al. | |
| 10,881,536 B2 * | 1/2021 | Noda | B25J 13/085 |
| 2006/0155386 A1 | 7/2006 | Wells et al. | |
| 2007/0213842 A1 * | 9/2007 | Simmons | A61F 2/68 623/64 |
| 2014/0196562 A1 * | 7/2014 | Takahashi | B25J 18/04 74/490.06 |
| 2019/0343662 A1 * | 11/2019 | Song | A61F 2/586 |

FOREIGN PATENT DOCUMENTS

| | | | | |
|---|---|---|---|---|
| CN | 105965536 A | * | 9/2016 | |
| CN | 106038175 A | * | 10/2016 | A61H 1/0218 |
| CN | 106980367 A | | 7/2017 | |
| CN | 108491077 A | | 9/2018 | |
| CN | 108983973 A | | 12/2018 | |
| CN | 109009586 A | * | 12/2018 | A61B 5/0488 |
| CN | 109464227 A | | 3/2019 | |
| CN | 109866250 A | | 6/2019 | |
| CN | 209004339 U | | 6/2019 | |
| CN | 109464227 B | * | 6/2021 | A61F 2/58 |
| WO | WO-2018178420 A1 | * | 10/2018 | A61F 2/54 |

OTHER PUBLICATIONS

English translation of Description section of Chinese patent CN104997579 (Year: 2015).*
English translation of Description section of Chinese patent CN109009586 (Year: 2018).*
English translation of Description section of Chinese patent CN109464227 (Year: 2019).*
English translation of Description section of Chinese patent CN109866250 (Year: 2020).*
Written Opinion of PCT/CN2020/094132. (Year: 2020).*
English translation of Description section of CN-209004339U. (Year 2019) (Year: 2019).*
English translation of the Description of CN-109866250 (Year: 2018).*

* cited by examiner

MULTI-DEGREE-OF-FREEDOM MYOELECTRIC ARTIFICIAL HAND CONTROL SYSTEM AND METHOD FOR USING SAME

TECHNICAL FIELD

The present disclosure relates to an artificial hand control system and a method for using same, and more particularly relates to a multi-degree-of-freedom myoelectric artificial hand control system and a method for using same.

BACKGROUND

Research on artificial prostheses can be applied to many fields such as high-end medical equipment, bio-mechatronic integrated intelligent robots, hazardous environment surveys, disaster rescue equipment, national defense equipment, and aiding disabled people in rehabilitation engineering training; and its scientific and technological achievements can be radiated, thus being of strategic importance. So far, the single-degree-of-freedom hand structure of humanoid robots has been very mature, but the single degree of freedom cannot meet the need for flexibility of the simulated artificial hand. Moreover, there is no algorithm that can synchronously identify the gesture of the artificial hand and its strength, thus limiting the application of the artificial hand.

SUMMARY

Invention objectives: One objective of the present disclosure is to provide a multi-degree-of-freedom myoelectric artificial hand control system capable of identifying the gesture and its strength synchronously and implementing control in multiple degrees of freedom. The other objective of the present disclosure is to provide a method for using the system.

Technical solution: A multi-degree-of-freedom myoelectric artificial hand control system of the present disclosure includes a robotic hand, a robotic wrist, a stump receiving cavity, and a data processor, where the robotic hand and the stump receiving cavity are respectively mounted on two ends of the robotic wrist, a multi-channel myoelectric array electrode oversleeve is connected in the stump receiving cavity, and a control unit circuit board and a battery are connected to the multi-channel myoelectric array electrode oversleeve; the other end of the control unit circuit board is connected to the robotic hand and the robotic wrist; the data processor sends a surface electromyography signal collection instruction to the control unit circuit board so that the multi-channel myoelectric array electrode oversleeve collects the surface electromyography signal, and further processes the received data with a neural network, to generate a gesture prediction model.

The robotic wrist includes a bevel gear set mechanism, a belt pulley drive mechanism, a servo motor, and a wrist support frame; the bevel gear set mechanism is formed by four mutually engaged bevel gears arranged in a cross; the left and right two bevel gears are mounted on the wrist support frame and separately connected to a transmission wheel; and the belt pulley drive mechanism is connected on the transmission wheel and is connected to the servo motor. In the bevel gear set mechanism, two sun gears are set in the horizontal direction; each sun gear is connected to the corresponding transmission wheel via a driving shaft, and is fixed on the driving shaft via a sun gear top screw; the transmission wheel is fixed on the driving shaft via a transmission shaft top screw; in the vertical direction, a first planetary gear connected to the robotic hand is located on the top, and a second planetary gear is located on the bottom, where a hollow driven shaft passes between the first planetary gear and the second planetary gear. A deep groove bearing is mounted between the hollow driven shaft and the first planetary gear, and between the hollow driven shaft and the second planetary gear. The wrist support frame is formed by a left plate, a right plate, a beam, and a bottom plate; the left and right plates are connected on the upper ends via the beam, and their lower ends are fixedly connected to the bottom plate; and the servo motor is mounted on the left and right plates, and a servo motor belt pulley is joined to the transmission wheel via a belt. A pinch roller is secured outside the belt.

A method of using the multi-degree-of-freedom myoelectric artificial hand control system of the present disclosure includes the following steps:

(S1) a user wearing the multi-channel myoelectric array electrode oversleeve, and then connecting the control unit circuit board and the battery;

(S2) the user completing gestures according to an experimental movement sequence; the data processor sending a surface electromyography signal collection instruction to the control unit circuit board; and the control unit circuit board controlling the multi-channel myoelectric array electrode oversleeve to collect the surface electromyography signal and then store the signal in the control unit circuit board, and uploading it to the data processor;

(S3) the data processor receiving the surface electromyography signal and inputting the signal into a neural network algorithm, to generate a gesture prediction model; and (S4) the user wearing the stump receiving cavity, connecting the robotic hand and the robotic wrist, and identifying gestures in real time by using the generated gesture prediction model; and the control unit circuit board controlling the multi-degree-of-freedom movement of the wrist and the robotic hand.

Data processing by the neural network algorithm in step S3 includes the following sub-steps:

(S31) preprocessing an original surface electromyography signal so as to extract a muscle activation signal, and then segmenting the activation signal by using a time window with a fixed length and using the segmented signals as an input layer of an unsupervised neural network; and the first hidden layer of the network compressing time-space features by means of principal component analysis;

(S32) the second hidden layer using an auto-encoder to learn 2N mutually synergistic muscle signal features obtained when forearm muscles complete different gestures, and generating continuous gesture labels according to the muscle synergy features and the experimental movement sequence, where 2N denotes 2N degrees of freedom of gestures to be identified, and N is the number of mutually antagonistic muscles in the forearm muscles involved in the gesture movement; and (S33) the third hidden layer fitting the muscle synergy features with the continuous gesture labels to generate a regression network, where an output layer of the regression network contains N neurons which respectively output continuous kinematic and kinetic data exhibited by N pairs of antagonistic muscles, different neurons represent different gestures, and the continuous data output by the neurons indicates the strength of the gestures.

Beneficial effects: The present disclosure has significant advantages compared to the prior art: 1. Continuous gestures and the gesture strength can be identified. 2. Multi-degree-of-freedom gestures can be made and the artificial hand is more flexible.

DETAILED DESCRIPTION OF THE EMBODIMENTS

Figure 1:
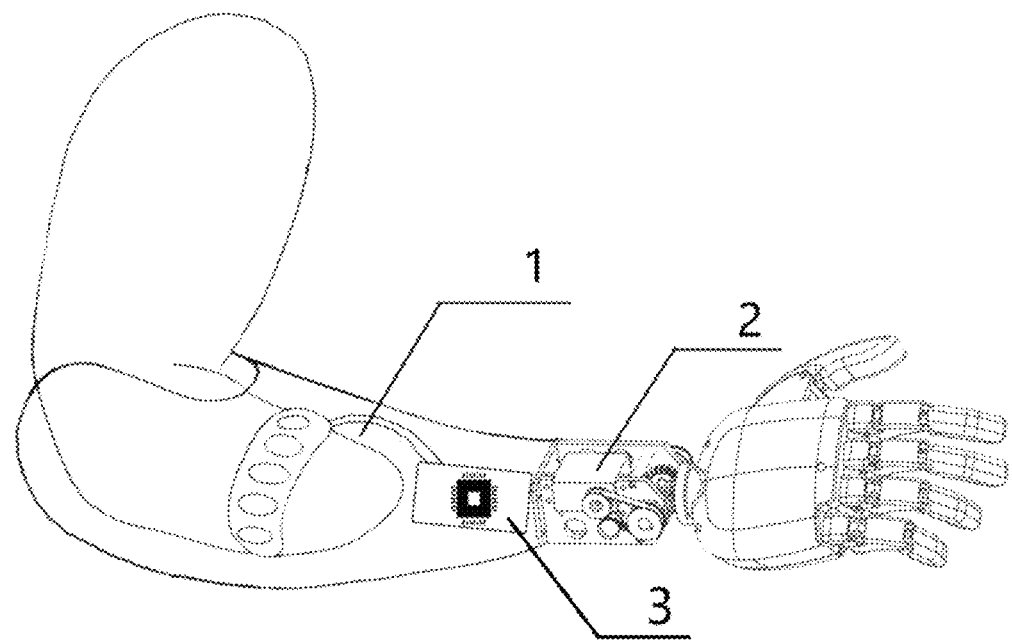
FIG. 1 is a schematic assembled diagram of an artificial hand of the present disclosure.
Figure 2:
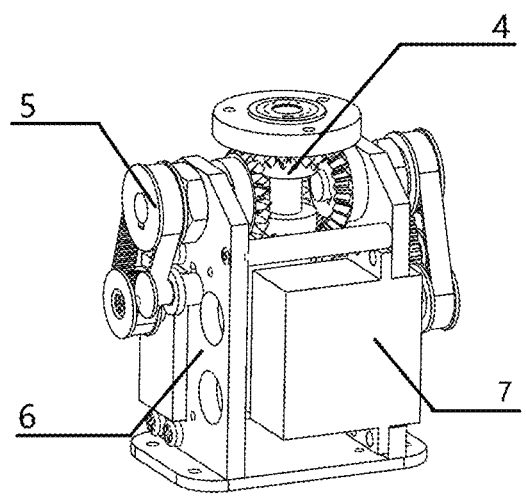
FIG. 2 is a schematic diagram of a wrist structure.
Figure 3:
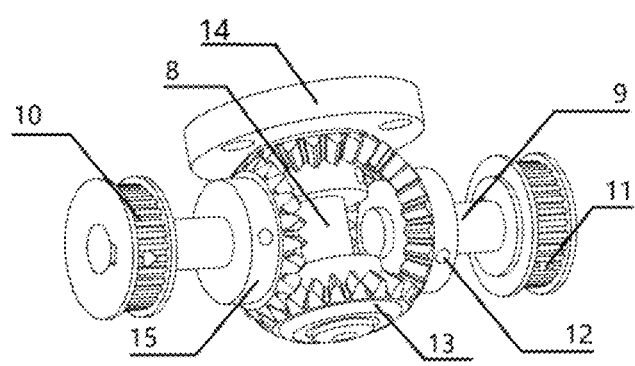
FIG. 3 is a schematic structural diagram of a bevel gear set mechanism.
Figure 4:
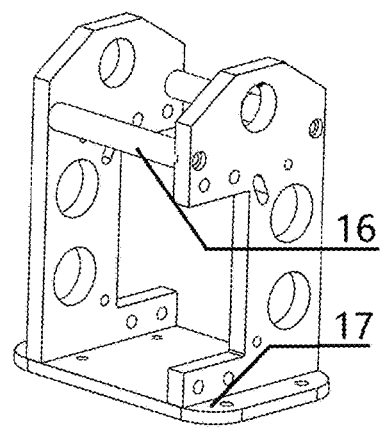
FIG. 4 is a schematic structural diagram of a wrist support frame.
Figure 5:
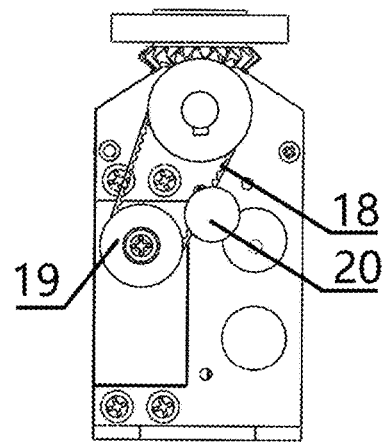
FIG. 5 is a side view of the wrist structure.

As shown from FIGS. 1 to 5, a multi-degree-of-freedom myoelectric artificial hand control system includes a robotic hand, a robotic wrist 2, a stump receiving cavity 1, and a data processor 3, where the robotic hand and the stump receiving cavity are respectively mounted on two ends of the robotic wrist. A multi-channel myoelectric array electrode oversleeve is connected in the stump receiving cavity, and a control unit circuit board and a battery are connected to the multi-channel myoelectric array electrode oversleeve; and the other end of the control unit circuit board is connected to the robotic hand and the robotic wrist. The data processor 3 sends a surface electromyography signal collection instruction to the control unit circuit board so that the multi-channel myoelectric array electrode oversleeve collects the surface electromyography signal; and further processes the received data with a neural network, to generate a gesture prediction model.

The robotic wrist 2 includes a bevel gear set mechanism 4, a belt pulley drive mechanism 5, a servo motor 7, and a wrist support frame 6. The bevel gear set mechanism 4 is formed by four mutually engaged bevel gears arranged in a cross. Two sun gears 15 are set in the horizontal direction and mounted on the wrist support frame 6. Each sun gear 15 is connected to a transmission wheel 10 via a driving shaft 9, and is fixed on the driving shaft 9 via a sun gear top screw 12. The transmission wheel 10 is fixed on the driving shaft 9 via a transmission shaft top screw 11. In the vertical direction, a first planetary gear 14 connected to the robotic hand is located on the top, and a second planetary gear 13 is located on the bottom, where a hollow driven shaft 8 passes between the first planetary gear 14 and the second planetary gear 13, and a deep groove bearing is mounted between the hollow driven shaft 8 and the first planetary gear 14, and between the hollow driven shaft 8 and the second planetary gear 13. The wrist support frame 6 is formed by a left plate, a right plate, a beam 16, and a bottom plate 17, where the left and right plates are connected on the upper ends via the beam 16, and their lower ends are fixedly connected to the bottom plate. The servo motor 7 is mounted on the left and right plates, and a servo motor belt pulley 19 is joined to the transmission wheel 10 via a belt 18. A pinch roller 20 is secured outside the belt 18.

Figure 6:
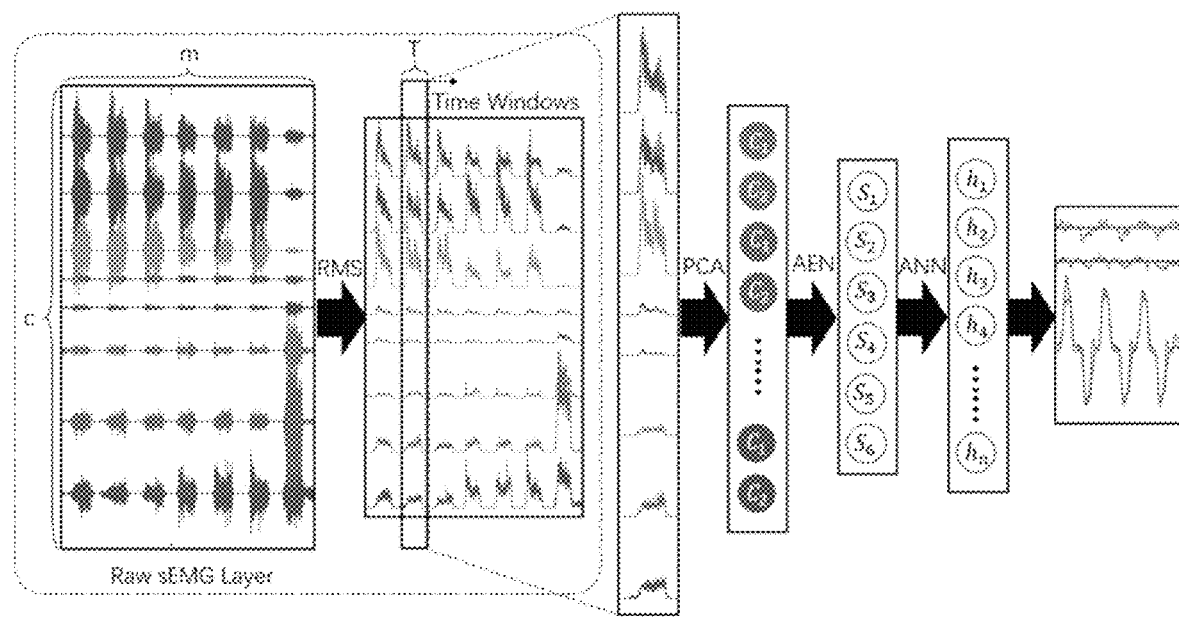
FIG. 6 is a block diagram of a hierarchical neural network.
Figure 9:
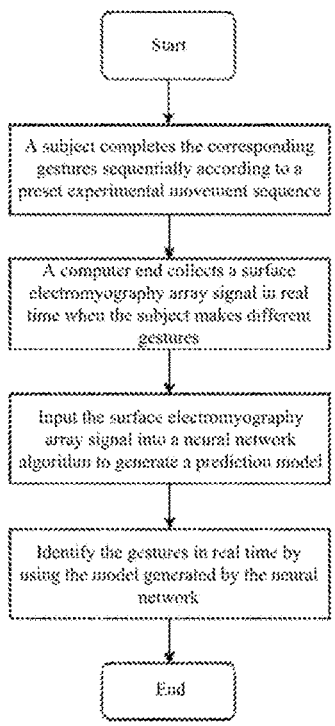
FIG. 9 is a flowchart of the gesture recognition algorithm.
Figure 10:
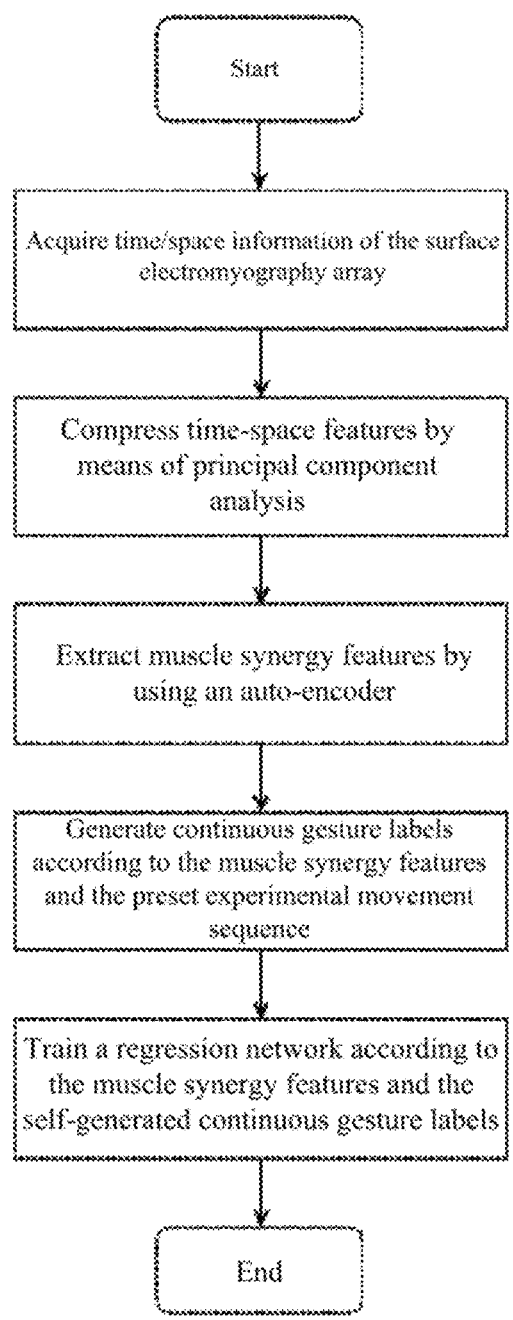
FIG. 10 is a flowchart of a neural network.

A procedure of a gesture recognition algorithm is shown by FIG. 9. During use, first, the control unit circuit board, the battery, and the multi-channel myoelectric array electrode oversleeve are connected. Then, a user wears the multi-channel myoelectric array electrode oversleeve, and completes a total of six movements in sequence: wrist outward turning, wrist outward rotation, hand opening, wrist inward turning, wrist inward rotation, and making a fist. These movements are based on three degrees of freedom movement: wrist turning, wrist rotation, and hand opening and closing; and each movement lasts for 3 seconds from beginning to end. Afterwards, the hand relaxes for 3 seconds. Each gesture should be completed 3 times in a row before making the next gesture, and a round of collection ends after all the gestures are completed. Three rounds of data collection are required for the same object. After the multi-channel myoelectric array electrode oversleeve collects the myoelectric signal, the signal is stored in the control unit circuit board and uploaded to the data processor 3, and then is input into a neural network algorithm for processing, where a processing procedure is shown by FIG. 10. After collection completion of the myoelectric data, a training set is processed by three layers of a hierarchical neural network. As shown in FIG. 6, first, original myoelectric signals from eight channels are preprocessed, and activation signals are acquired by means of Root Mean Square (RMS). Then, the eight activation signals are segmented by a time window with a fixed length, and the segmented signals are used as an input layer of the neural network, where each input sample contains space and time information of the array myoelectric signal. The first hidden layer of the network reduces the dimension of the input signal by means of principal component analysis; the second hidden layer uses an auto-encoder to learn six muscle synergy features to further reduce the feature dimension; and the third hidden layer fits the muscle synergy features with automatically generated movement intention labels. A final network output layer contains three neurons which respectively output continuous movement data in three degrees of freedom. The weight matrices of the hidden layers of the neural network are trained independently and then stacked together, and fine tuning is performed layer by layer during actual fitting by the deep neural network, where predicted wrist movement information is used for controlling the robotic wrist 2, and hand opening and closing information is used for controlling the robotic hand mounted on the robotic wrist 2.

It is set that the time window in FIG. 6 contains T sample points and the number of array myoelectric sensors is c, and then the number of neurons in the network input layer is c×T. In order to acquire representative time and space information from redundant information, the present disclosure performs principal component analysis at the time scale for the electromyography activation signal in each channel, and uses the T electromyography activation signal sampling points in the time window as features introduced into the principal component analysis, to generate samples by means of a sliding window. A sliding stride is set to 1, and the number of sampling points of the surface electromyography signal in a single channel is set to m. Then, the number of the generated samples is m−T+1. FIG. 6 illustrates that two principal components are selected for each electromyography signal channel to represent the data in the time window.

Figure 7:
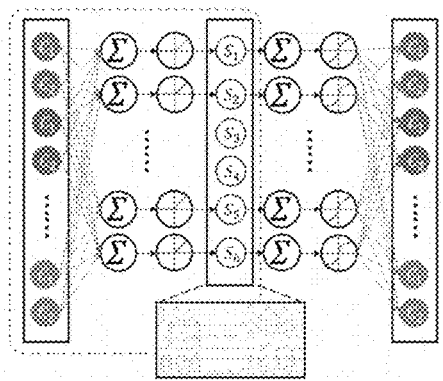
FIG. 7 is a block diagram of an auto-encoder in the first hidden layer of a gesture recognition algorithm.

FIG. 7 shows a process of the second hidden layer in FIG. 6 extracting 2N muscle synergy features from the principal component features in the eight channels, where 2N denotes 2N degrees of freedom of gestures to be identified, and N is the number of mutually antagonistic muscles in the forearm muscles involved in the gesture movement. After processing by the first-layer network, the number of neurons continuously input to the neural network is reduced from c×T to c×2. Further, the neurons in the second layer are used for extracting features related to muscle synergy. In this embodiment, six muscle synergy features are extracted from electromyography activation features, which are respectively corresponding to wrist outward turning, wrist inward turning, clockwise wrist rotation, counterclockwise wrist rotation, hand opening, and making a fist. Values of the muscle synergy features are all non-negative. A weight matrix of the neurons in the second layer is obtained by training an auto-encoder. The main characteristic of the auto-encoder is that the input neurons are totally identical to the output neurons, and the number of neurons in the hidden layer is less than the number of the input and output neurons. Such a neural network structure can obtain some underlying features of the input data. An encoding process is from the input layer to the hidden layer of the network, and a decoding process is from the hidden layer to the output layer. The present disclosure uses the encoded part after training completion of the auto-encoder as a weight matrix of the first-layer network. In order that the neurons in the hidden layer are all non-negative, the Relu function is used as the activation function in the encoding process. Because of the characteristic that the numerical values contained in the input layer are negative, in order that the output layer can recover negative values, the Tanh function is used as the activation function in the decoding process. The cross entropy function is used as the loss function of the auto-encoder. The weight matrix of the encoder is initialized by means of Xavier, which can enable the initial weights to be normally distributed with a mean of 0. Overfitting is reduced in an iterative training process by means of the pruning algorithm. A network learning rate decays exponentially with the number of iterations, and the training is accelerated by means of ADAM gradient descent and Mini-Batch. Compared to a non-negative matrix factorization method, the method of the present disclosure can obtain a fitted model with a better approximation effect due to subjection to operations with a nonlinear activation function.

Figure 8:
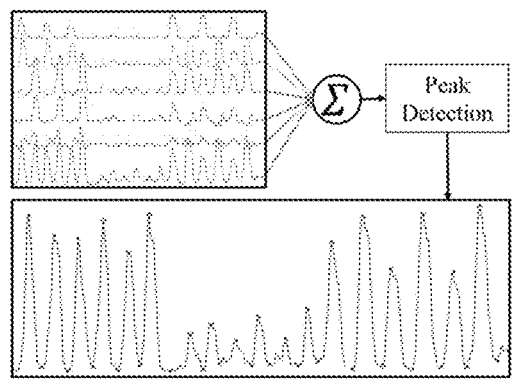
FIG. 8 is a schematic diagram of a label self-generation method.

FIG. 8 shows a process of extracting kinematic and kinetic labels from the muscle synergy features obtained in FIG. 7. Although expected movement intentions cannot be directly obtained from the muscle synergy features learned by the auto-encoder, when the six synergy features are subjected to a vector superposition operation, an oscillation waveform graph shown by FIG. 8 can be obtained, where each peak denotes a maximum value of a muscle synergy degree that is reached when a certain movement is done, and the troughs on the two sides indicate that the muscle synergy is at rest. Therefore, a complete trough-peak-trough section indicates a process of completing a certain gesture to the strongest degree of muscle activation and then to the rest and recovery status. Thus, kinematic parameter labels for a total of three degrees of freedom of the hand and wrist can be reconstructed by searching for the positons of the peaks and troughs. After the label data is obtained, finally, the muscle synergy features calculated by the previous-layer network and the label data are introduced into a feedforward neural network for regression fit. An obtained network layer and network layers calculated in the previous two steps are stacked, to form a final deep regression model. All the network layers are trained and then stacked to form a final gesture recognition network which is then fed back to the control unit circuit board. During actual use, a user wears the stump receiving cavity 1, connects the robotic hand and the robotic wrist 2, and controls the wrist and hand movements of the artificial hand by imagining gesture movements. The control unit circuit board controls the multi-degree-of-freedom movement of the robotic wrist 2 and the robotic hand of the prosthesis simultaneously, and the movement speed of the robotic hand is adjusted and controlled according to the muscle strength predicted by the hierarchical network.

What is claimed is:

1. A multi-degree-of-freedom myoelectric artificial hand control system, comprising: a robotic hand, a robotic wrist, a stump receiving cavity, and a data processor, wherein the robotic hand and the stump receiving cavity are respectively mounted on two ends of the robotic wrist, a multi-channel myoelectric array electrode oversleeve is connected in the stump receiving cavity, and a control unit circuit board and a battery are connected to the multi-channel myoelectric array electrode oversleeve; the other end of the control unit circuit board is connected to the robotic hand and the robotic wrist; the data processor sends a surface electromyography signal collection instruction to the control unit circuit board so that the multi-channel myoelectric array electrode oversleeve collects the surface electromyography signal, and further receives data and processes the data, to generate a gesture prediction model, wherein the robotic wrist comprises a bevel gear set mechanism, a belt pulley drive mechanism, a servo motor, and a wrist support frame; the bevel gear set mechanism is formed by four mutually engaged bevel gears arranged in a cross; two of the bevel gears positioned on a horizontal direction are mounted on the wrist support frame and separately connected to a transmission wheel; and the belt pulley drive mechanism is connected on the transmission wheel and is connected to the servo motor.

2. The multi-degree-of-freedom myoelectric artificial hand control system according to claim 1, wherein in the bevel gear set mechanism, two sun gears are set in the horizontal direction; each sun gear is connected to the corresponding transmission wheel via a driving shaft, and is fixed on the driving shaft via a sun gear top screw; the transmission wheel is fixed on the driving shaft via a transmission shaft top screw; in a vertical direction, a first planetary gear having a top surface connected to the robotic hand, and a second planetary gear is located in the vertical direction to face the first planetary gear, wherein a hollow driven shaft passes between the first planetary gear and the second planetary gear.

3. The multi-degree-of-freedom myoelectric artificial hand control system according to claim 2, wherein a deep groove bearing is mounted between the hollow driven shaft and the first planetary gear, and between the hollow driven shaft and the second planetary gear.

4. The multi-degree-of-freedom myoelectric artificial hand control system according to claim 1, wherein the wrist support frame is formed by a left plate, a right plate, a beam, and a bottom plate; the left and right plates are connected on the upper ends via the beam, and their lower ends are fixedly connected to the bottom plate; the servo motor is mounted on the left and right plates, and a servo motor belt pulley is joined to the transmission wheel via a belt.

5. The multi-degree-of-freedom myoelectric artificial hand control system according to claim 4, wherein a pinch roller is secured outside the belt.

6. A method of using a multi-degree-of-freedom myoelectric artificial hand control system comprising: a robotic hand, a robotic wrist, a stump receiving cavity, and a data processor, wherein the robotic hand and the stump receiving cavity are respectively mounted on two ends of the robotic wrist, a multi-channel myoelectric array electrode oversleeve is connected in the stump receiving cavity, and a control unit circuit board and a battery are connected to the multi-channel myoelectric array electrode oversleeve; the other end of the control unit circuit board is connected to the robotic hand and the robotic wrist; the data processor sends a surface electromyography signal collection instruction to the control unit circuit board so that the multi-channel myoelectric array electrode oversleeve collects the surface electromyography signal, and further receives data and processes the data, to generate a gesture prediction model, the method comprising the following steps:

- (S1) a user wearing the multi-channel myoelectric array electrode oversleeve, and then connecting the control unit circuit board and the battery;
- (S2) the user completing gestures according to an experimental movement sequence; the data processor sending a surface electromyography signal collection instruction to the control unit circuit board; and the control unit circuit board controlling the multi-channel myoelectric array electrode oversleeve to collect the surface electromyography signal and then store the signal in the control unit circuit board, and uploading it to the data processor;
- (S3) the data processor receiving the surface electromyography signal and inputting the signal into a neural network algorithm, to generate a gesture prediction model; and
- (S4) the user wearing the stump receiving cavity, connecting the robotic hand and the robotic wrist, and identifying gestures in real time by using the generated gesture prediction model; and the control unit circuit board controlling the multi-degree-of-freedom movement of the wrist and the robotic hand.

7. The method of using the multi-degree-of-freedom myoelectric artificial hand control system according to claim 6, wherein data processing by the neural network algorithm in step S3 comprises the following sub-steps:

- (S31) preprocessing an original surface electromyography signal so as to extract a muscle activation signal, and then segmenting the activation signal by using a time window with a fixed length and using the segmented signals as an input layer of an unsupervised neural network; a first hidden layer of the network compressing time-space features by means of principal component analysis;
- (S32) a second hidden layer using an auto-encoder to learn 2N mutually synergistic muscle signal features obtained when forearm muscles complete different gestures, and generating continuous gesture labels according to muscle synergy features and the experimental movement sequence, wherein 2N denotes 2N degrees of freedom of gestures to be identified, and N is the number of mutually antagonistic muscles in forearm muscles involved in the gesture movement; and
- (S33) a third hidden layer fitting the muscle synergy features with the continuous gesture labels to generate a regression network, wherein an output layer of the regression network contains N neurons which respectively output continuous kinematic and kinetic data exhibited by N pairs of antagonistic muscles, different neurons represent different gestures, and the continuous data output by the neurons indicates the strength of the gestures.

* * * * *